(12) United States Patent
Deane

(10) Patent No.: US 9,180,452 B2
(45) Date of Patent: Nov. 10, 2015

(54) MICROFLUIDIC RESISTANCE NETWORK AND MICROFLUIDIC DEVICE

(75) Inventor: Steven Charles Deane, Eindhoven (GB)

(73) Assignee: KONINKLIJKE PHILIPS N.V., Eindhoven (NL)

(*) Notice: Subject to any disclaimer, the term of this patent is extended or adjusted under 35 U.S.C. 154(b) by 255 days.

(21) Appl. No.: 13/985,375

(22) PCT Filed: Feb. 14, 2012

(86) PCT No.: PCT/IB2012/050654
§ 371 (c)(1),
(2), (4) Date: Aug. 14, 2013

(87) PCT Pub. No.: WO2012/110943
PCT Pub. Date: Aug. 23, 2012

(65) Prior Publication Data
US 2013/0320999 A1 Dec. 5, 2013

(30) Foreign Application Priority Data
Feb. 18, 2011 (EP) .................................. 11154993

(51) Int. Cl.
*B01L 3/00* (2006.01)
*G01N 1/18* (2006.01)
(Continued)

(52) U.S. Cl.
CPC ..... *B01L 3/502746* (2013.01); *B01L 3/502776* (2013.01); *B01L 2300/0816* (2013.01);
(Continued)

(58) Field of Classification Search
CPC ............... B01L 3/502746; B01L 3/502769; B01L 3/502776; B01L 2300/0816; B01L 2300/0864; B01L 2300/0867; B01D 9/004; B01D 9/04; B01D 17/00; G01N 35/08; G01N 2001/383; Y10T 137/85938
USPC ............ 324/649, 600; 422/50, 402, 408, 412, 422/417, 82.01, 82.02; 436/149, 150, 177, 436/179
See application file for complete search history.

(56) References Cited

U.S. PATENT DOCUMENTS 4,946,795 A 8/1990 Gibbons
5,858,195 A 1/1999 Ramsey
(Continued)

FOREIGN PATENT DOCUMENTS

WO WO2009039283 A1 3/2009
WO WO2010086786 A1 8/2010

OTHER PUBLICATIONS

Cheung K. et al., "Impedance Spectroscopy Flow Cytometry: On-Chip Label-Free Cell Differentiation", Cytometry. Part A, John Wiley, Hoboken, NJ, US, vol. 65A, Jan. 1, 2005, pp. 124-132, XP002534498.

*Primary Examiner* — Hoai-An D Nguyen
(74) *Attorney, Agent, or Firm* — Larry Liberchuk

(57) ABSTRACT

A microfluidic resistance network (20) is disclosed that comprises a first microfluidic channel (112) in fluidic communication with a first fluid inlet (22); and a second microfluidic channel (114) in fluidic communication with a second fluid inlet (24); wherein the microfluidic resistance network (20) further comprises a cross-shaped dilution stage (100) having the first microfluidic channel (112) as a first dilution stage inlet and the second microfluidic channel (114) as a second dilution stage inlet, the dilution stage further comprising a first microfluidic outlet channel (122) for combining a portion of a first fluid from the first microfluidic channel with a second fluid from the second microfluidic channel (114) and a second microfluidic outlet channel (124) for receiving the remainder of first fluid. A microfluidic device (200) comprising such a microfluidic resistance network (20) is also disclosed.

15 Claims, 5 Drawing Sheets

Figure 1:
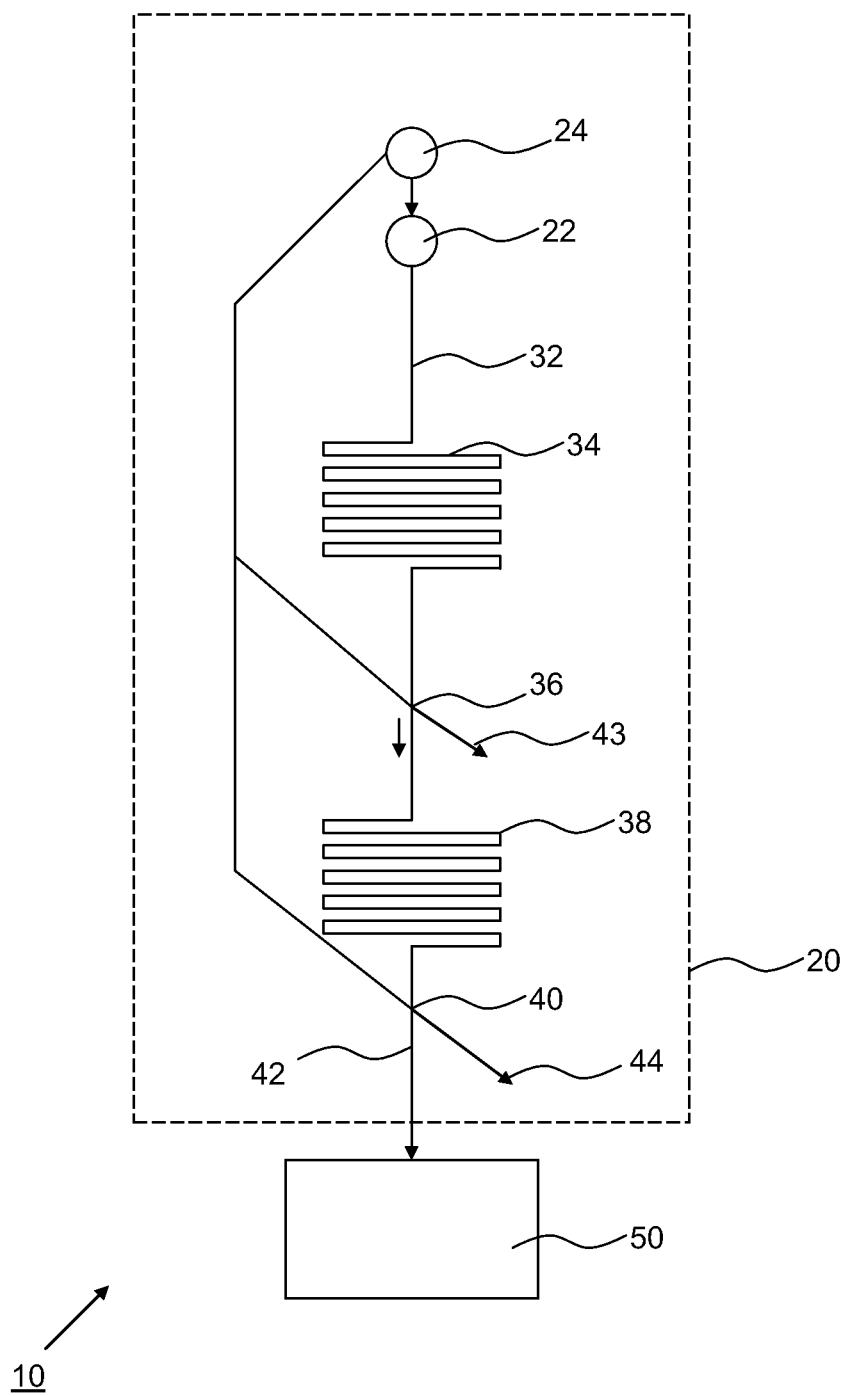

(51) Int. Cl.
*G01N 35/08* (2006.01)
*G01N 1/38* (2006.01)

(52) U.S. Cl.
CPC .. *B01L2300/0864* (2013.01); *B01L 2300/0867* (2013.01); *G01N 35/08* (2013.01); *G01N 2001/383* (2013.01); *Y10T 137/85938* (2015.04)

(56) References Cited

U.S. PATENT DOCUMENTS

| | | |
|---|---|---|
| 5,972,710 A | 10/1999 | Weigl |
| 6,004,515 A | 12/1999 | Parce |
| 6,062,261 A | 5/2000 | Jacobson |
| 6,506,609 B1 | 1/2003 | Wada |
| 7,060,171 B1 | 6/2006 | Nikiforov |
| 8,642,353 B2 * | 2/2014 | Welle .............. 436/177 |
| 2003/0175944 A1 | 9/2003 | Yang |
| 2004/0203136 A1 | 10/2004 | Kellogg |
| 2006/0108012 A1 | 5/2006 | Barrow |
| 2008/0254541 A1 | 10/2008 | Kang |
| 2009/0123337 A1 | 5/2009 | Noda |
| 2010/0072068 A1 | 3/2010 | Doyle |
| 2014/0346045 A1 * | 11/2014 | Chi et al. .......... 204/547 |

* cited by examiner

MICROFLUIDIC RESISTANCE NETWORK AND MICROFLUIDIC DEVICE

FIELD OF THE INVENTION

The present invention relates to a micro fluidic resistance network comprising a first microfluidic channel in fluidic communication with a sample inlet; and a second microfluidic channel in fluidic communication with a diluent inlet.

The present invention further relates to a microfluidic device comprising such a microfluidic resistance network.

BACKGROUND OF THE INVENTION

In healthcare, there is a trend towards the development of so-called Point of Care (POC) devices, which are small devices, often with disposable components such as cartridges, that can be used in diagnosis and treatment of patients as an alternative to large and expensive analysis equipment.

A widely used diagnostic test is a Full blood count (FBC) test, which is a diagnostic test that is used to measure cellular composition of blood. It may give information about the status of an immune system of a patient, about the ability of the blood to disseminate oxygen and/or about the ability of the blood to effectively clot. As such, it is a fundamental test that is often used as an initial "general purpose" diagnostic tool or as a more targeted monitoring solution. Examples of care cycles that include a full blood count as a monitoring tool include oncology, arthritis and Crohn's disease. As many as 300 million FBC tests are performed each year in the developed world. FBC tests may further be used in chemotherapy monitoring, veterinary blood analysis applications and so on.

Currently, large scale commercial laboratory instruments known as hematology analyzers are used to automatically perform all measurements that comprise the FBC. The high cost and complexity of these devices, coupled to the need for venous blood, means that they are mostly large scale, centralized facilities. There is a clear clinical need for performing FBC in a near patient setting, particularly for applications that require a full blood count to monitor the progression and/or treatment of a disease.

Previously, microfluidic point of care devices have been developed which are capable of measuring individual components of the FBC. In that area, Hb measuring devices, WBC counters capable of performing a white blood cell differential and platelet count devices, devices which optically count and determine size of red blood cells are available. For cell counting, current hematology analyzers typically employ electrical coulter counting and/or optical scattering methods to count and differentiate white cells and to count and determine size of the red blood cells and platelets.

At the moment only few examples of micro fluidic coulter counter technologies exist. One example combines a coulter counter with a Hb measurement. Another example of counting cells is by flow-through impedance spectroscopy. This is a flow cytometry analysis which is especially suited for a micro fluidic format. This technique is capable of differentiating between lymphocytes, monocytes and neutrophils in lysed blood, and of counting and sizing red blood cells and platelets.

The current "gold-standard" for Hb measurement is the photometric cyanmethaemoglobin (HbCN) method disclosed in Standardization of hemoglobinometry II, The hemiglobincyanide method, Clin Chim Acta, 1961, 6, p. 38-44. This method involves chemical lysis of the red blood cells and subsequent labelling of all the Hb that these cells release with a cyanide ion. The labels produce a defined absorption profile with a maximum at 540 nm. By measuring the optical absorption at 540 nm, the concentration of Hb can be determined. Furthermore, the high stability of HbCN means that it is easy to supply a calibration standard.

The most common red blood cell lysis/cyanide conversion reagent is known as Drabkin's reagent. Drabkin's reagent contains Potassium Cyanide, which is extremely toxic. This reagent only works for very large dilutions in whole blood (1:251), since red blood cell lysis relies on the low ionic strength of the reagent to induce osmotic shock. This large dilution causes an inherent imprecision in the method. Furthermore, to measure the optical absorption at 540 nm, very long optical path lengths of ~1 cm are required. Finally, in some pathological samples, turbidity can lead to erroneously high absorption readings, which in turn will give rise to an incorrect Hb concentration.

To avoid the problems associated with toxicity and turbidity, many other optical means of measuring Hb have been developed. A known point of care device uses sodium azide to convert the Hb to an azide-coordinated Hb derivative (azidemethemoglobin, $HbN_3$). This method itself lends to short path length (0.1 mm) absorption spectroscopy, since dry reagents remove the need for dilution of the whole blood. Two absorbance readings are taken to determine the $HbN_3$ concentration, i.e. one at the absorption maximum (565 nm) and one at 800 nm to correct for turbidity.

For the point of care WBC/Hb counter, a RBC lysis solution has been developed that preserves the WBCs while at the same time labeling the Hb molecule with imidazole. In a similar way as described above, the optical absorption of the imidazole labeled Hb species is measured at two wavelengths, i.e. one at the absorption peak and one to correct for turbidity and scattering effects for the white blood cells. The same solution may also be passed through a coulter counter to perform the cell count.

Another known lysis/Hb conversion reagent is based on sodium lauryl sulphate/sodium dodecyl sulphate (SLS/SDS). The SDS lyses all the blood cells and labels the Hb to get an SDS-coordinated derivative. Since SDS is a surfactant molecule, turbidity correction is not necessary and so a single absorption reading at 535 nm is taken to determine the Hb concentration. This method is designed for high dilutions of Hb, so the inherent imprecision present in the HbCN measurement is still present in the HbSDS one.

All the above described devices and techniques are capable of performing specific measurements from a finger-prick of blood. However, none of the above described devices and techniques are capable of measuring all parameters that are required for an FBC in a single POC measurement. Recently, a microfluidic device capable of performing a FBC in a single POC measurement has been disclosed in WO 2010/086786. This microfluidic device comprises a two sample preparation stages, one for diluting a portion of a blood sample with a lysis agent for a white blood cell count and a quench solution and providing the diluted portion to an impedance measurement means and a second dilution stage for diluting a further portion of the blood sample with a diluent for hemoglobin measurement and providing the diluted further portion to a measurement means for determining properties of red blood cells, such as RBC count, HB count and platelet count. The diluent is fed to the blood sample several times (i.e. at different points in the microfluidic network) to obtain a high dilution ratio. Consequently, only a fraction of the RBC count sample is used for the actual RBC count, with well over 90% of the various dilution stages being fed to waste.

In resistive microfluidic networks such as present in the microfluidic device disclosed in WO 2010/086786, dilution of the sample is achieved by providing a branch between a microfluidic channel transporting the sample and a microfluidic channel transporting a diluent, such as a lysing agent or a quenching solution. Consequently, a Y-shaped dilution stage is obtained having a main channel (the diluent channel) and a secondary channel branching into the main channel (the branch off the sample channel). Such Y-shaped branches are also used to branch off a small fraction of a diluted sample for further dilution, whilst the bulk of the diluted sample is fed to waste.

In order to achieve the required dilution ratio, it is possible in theory that the dimensions of the respective microfluidic channels are tuned to reduce the volume passing through the channel during a given time period. However, for most manufacturing processes, it is not practically feasible to reduce the dimensions of such a channel to below certain limits dictated by the manufacturing process. In such situations, to achieve the branching off of the correct amount of fluid, the flow rate through the branch has to be reduced, e.g. by tuning the fluidic resistance of the branch.

However, a problem associated with such low flow rates is that upon start-up of a fluidic flow through the resistive microfluidic network, bubbles can get trapped in those parts of the network that exhibit the low flow rate such as the aforementioned branch. This can significantly extend the duration of the initialization of the microfluidic device as such bubbles must be cleared from the device before the device is ready for use.

SUMMARY OF THE INVENTION

The present invention seeks to provide a resistive microfluidic network in which the risk of bubble trapping upon start-up is at least reduced.

The present invention further seeks to provide a microfluidic device comprising such a resistive micro fluidic network.

According to a first aspect of the present invention, there is provided a microfluidic resistance network comprising a first microfluidic channel in fluidic communication with a first inlet; and a second microfluidic channel in fluidic communication with a second inlet; wherein the micro fluidic resistance network further comprises a cross-shaped dilution stage having the first microfluidic channel as a first dilution stage inlet and the second microfluidic channel as a second dilution stage inlet, the first dilution stage inlet and the second dilution stage inlet forming a first junction, the dilution stage further comprising a first microfluidic outlet channel for providing a portion of the first fluid diluted with said second fluid and a second micro fluidic outlet channel for receiving the remainder of said first fluid, the first microfluidic outlet and the second micro fluidic outlet forming a second junction opposite the first junction.

The present invention is based on the recognition that a first fluid such as a sample can be accurately diluted in a X-shaped dilution stage in which the outlet channels are dimensioned such that the whole second fluid stream, e.g. a diluent stream and a fraction of the first fluid stream are fed into the first microfluidic outlet channel and the remainder of the first fluid stream is fed into the second microfluidic outlet channel. Consequently, as instead of branching off a channel from the first microfluidic channel tuned to a low flow rate e.g. to provide the dilution stage with a fraction of a sample, the whole first fluid volume is presented to the X-shaped dilution stage, the need for overly slow flowing channels is avoided, thus reducing the risk of bubble trapping. The appropriate amount of fluid branching off into the first microfluidic outlet channel and the second microfluidic outlet channel respectively may be achieved by tuning the pressure (resistance) in the micro fluidic resistance network.

In an embodiment, said first junction comprising a central point where the respective sidewalls of the first micro fluidic channel and the second microfluidic channel meet, wherein a imaginary axis through said central point dissects the angle between the first microfluidic channel and the second microfluidic channel; said second junction comprising a further central point where the respective sidewalls of the first microfluidic outlet channel and the second microfluidic outlet channel meet, the further central point being displaced with respect to said imaginary axis by a predefined distance.

The two fluid streams entering the X-shaped dilution stage remain separated from each other. The separation boundary is defined by the axis dissecting the first junction, i.e. the imaginary axis through the central point of the first junction that divides the angle between the first microfluidic channel and the second micro fluidic channel in two. By displacing the further central point of the second junction by a predefined distance with respect to this fluid stream boundary, the further central point lies inside the path of the first fluid stream, e.g. a sample stream, such that the further central point acts as a divider of the first fluid stream, dividing a main fraction of the first fluid into one of the outlet channels and the remainder of the first fluid together with the second fluid stream into the other of the outlet channels. This way, a very simple but accurate dilution of a fluid such as a sample is achieved. This embodiment is particularly useful for fluid streams having high flow rates, i.e. flow rates with Reynolds number $Re \geq 1$. For smaller flow rates, the same technical effect may be achieved by tuning of the pressure of the microfluidic resistance network as previously explained.

Advantageously, the cross-shaped dilution stage further comprises an intermediate section coupling the first junction to the second junction. Such an intermediate section may be used to ensure that an equilibrium flow profile is achieved between the first fluid flow and the second fluid flow.

Preferably, the intermediate section has a length extending from the first junction to the second junction such that the first fluid and the second fluid remain substantially separated from each other in said intermediate section as the residence time in the junction is small compared to the time for the fluids to significantly diffuse into each other. Consequently, the dilution ratio can be solely defined by the position of the central point of the second junction or by the tuning of the pressures of the microfluidic resistance network, thus simplifying the design of the dilution stage.

Preferably, the microfluidic resistance network is tuned such that in operation the ratio of the respective flow rates of the first fluid and the second fluid entering the cross-shaped dilution stage is in the range of 1:5-5:1. It has been found that if the dimensions of the first micro fluidic channel and the second microfluidic channel are chosen to produce flow rates outside this range the lower flow rate channel becomes more susceptible to bubble trapping at start-up of the resistive micro fluidic network.

In an embodiment, the first micro fluidic outlet channel is in fluidic communication with a mixing stage downstream from the cross-shaped dilution stage. Such a mixing stage ensures that the first fluid portion and the second fluid are properly mixed or that an intended reaction between the first fluid portion and the second fluid is completed at the outlet of the mixing stage, e.g. in case of a diluent comprising a lysing agent for lysing cellular material in the sample.

In a preferred embodiment, cross-shaped dilution stage is one of a chain of serially connected cross-shaped dilution stages, and wherein the second microfluidic channel comprises a plurality of branches, each of said branches providing one of the inlets of one of the cross-shaped dilution stages in said chain, wherein the other inlet of the first cross-shaped dilution stage in said chain is coupled to the first microfluidic channel, and the other inlet of each of the remaining cross-shaped dilution stages is coupled to the first microfluidic outlet channel of the previous cross-shaped dilution stage in said chain. This has the advantage that a high dilution ratio can be achieved for the sample by providing a diluent to a single inlet and feeding the diluent into multiple cross-shaped dilution stages to further dilute the sample in each of these stages. Such a microfluidic resistance network can for instance be used in a microfluidic device for a single step FBC analysis, such as the microfluidic device disclosed in WO 2010/086786.

The microfluidic resistance network of the present invention may be comprised in a disposable cartridge for a body fluid analysis system. As the micro fluidic resistance network may be manufactured at a relatively low cost, e.g. by realizing the microfluidic resistance network in a suitable polymer material, a multiple-use body fluid analysis system may be provided in an economically feasible manner. In an embodiment, the cartridge may further comprise a measurement chip for performing the desired measurement on the diluted sample.

In accordance with another embodiment of the present invention, there is provided a microfluidic device comprising a microfluidic resistance network according to an embodiment of the present invention; and a measurement device comprising a sample channel in fluidic communication with the first microfluidic outlet channel, the sample channel comprising measurement means. Such a microfluidic device benefits from reduced start-up times and lower risk of failure due to the reduced risk of bubble trapping in the microfluidic resistance network of the present invention.

In an embodiment, the measurement means comprise a first electrode pair and a second electrode pair downstream from the first electrode pair for performing an impedance measurement. Such measurement means are for instance suitable for performing a blood cell count, e.g. a RBC or WBC count, by means of an impedance measurement in case the sample is a blood sample.

In an embodiment, the micro fluidic device further comprises an optical measurement cell for measuring a hemoglobin count, such that the microfluidic device may be used for a single-step FBC analysis.

BRIEF DESCRIPTION OF THE EMBODIMENTS

Figure 2:
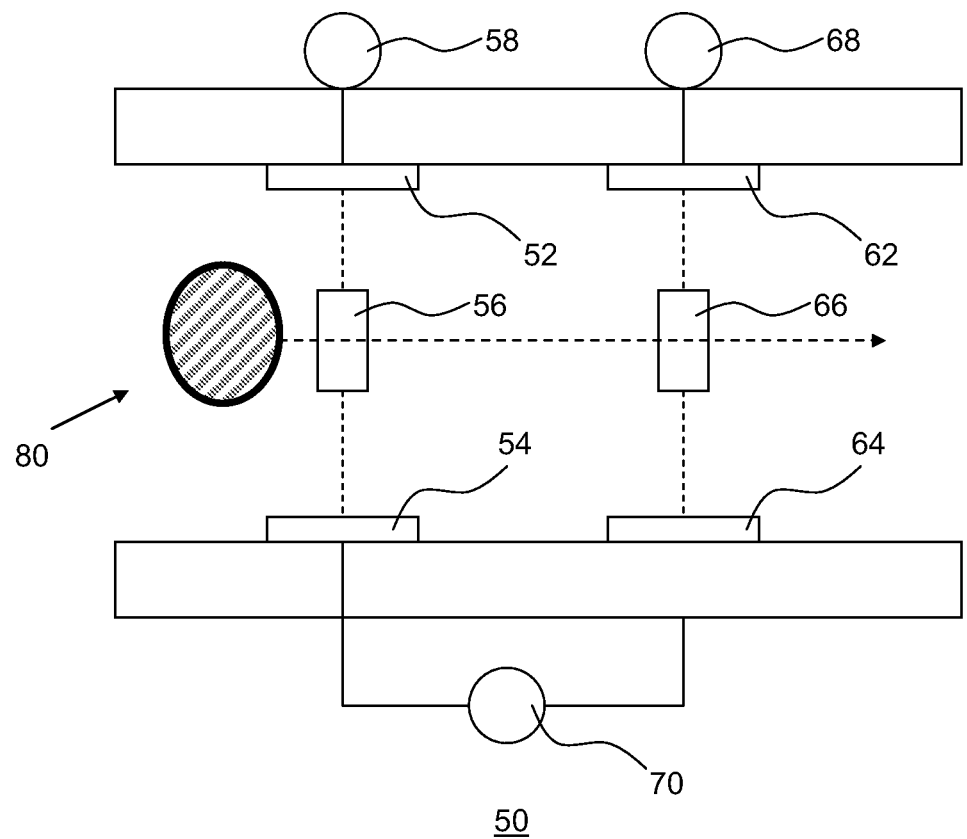
Figure 2:
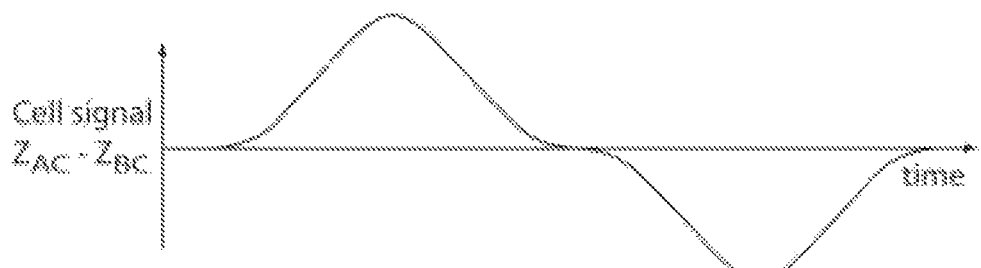
Figure 3:
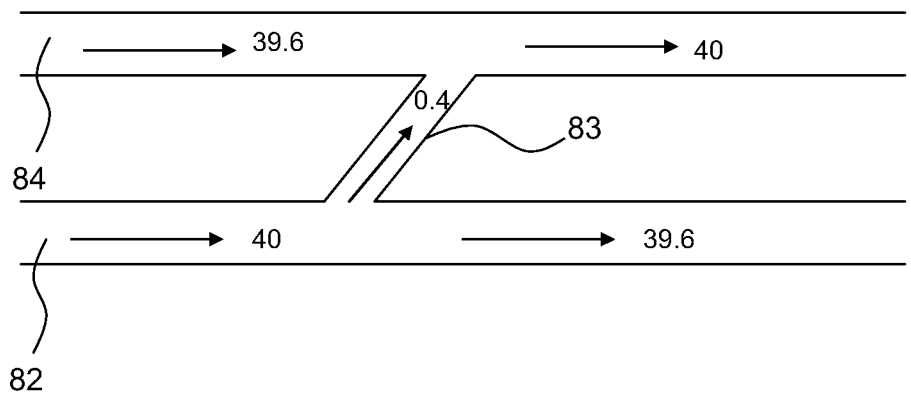
Figure 4:
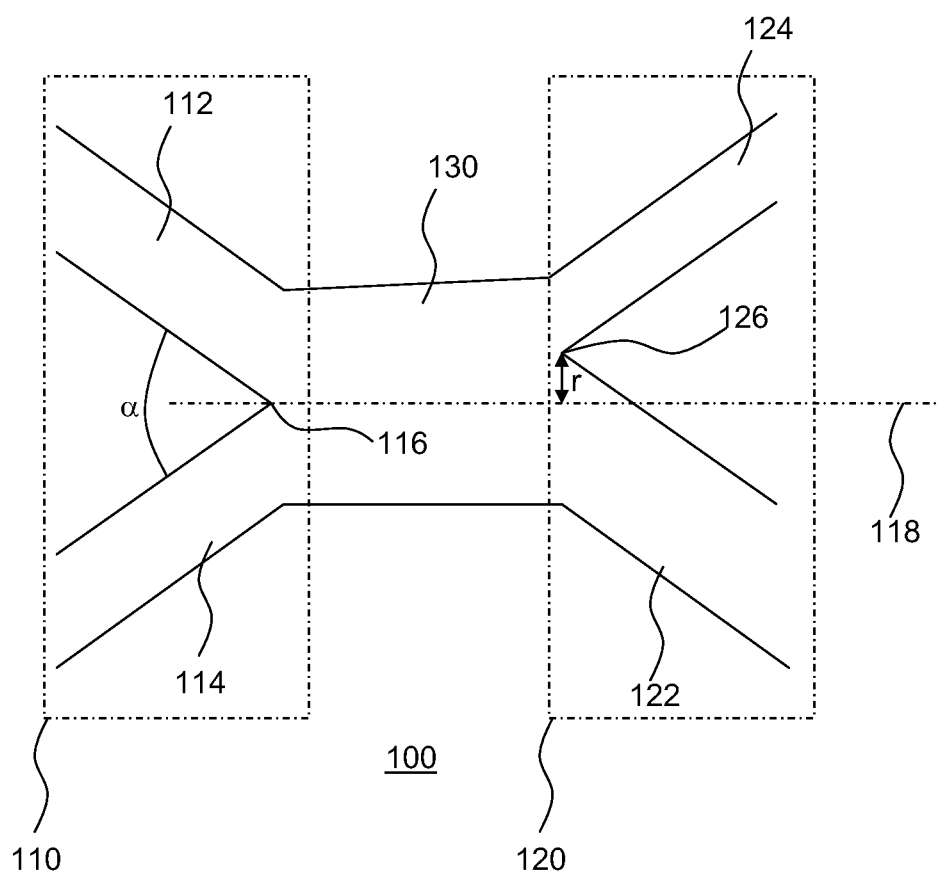
Figure 5:
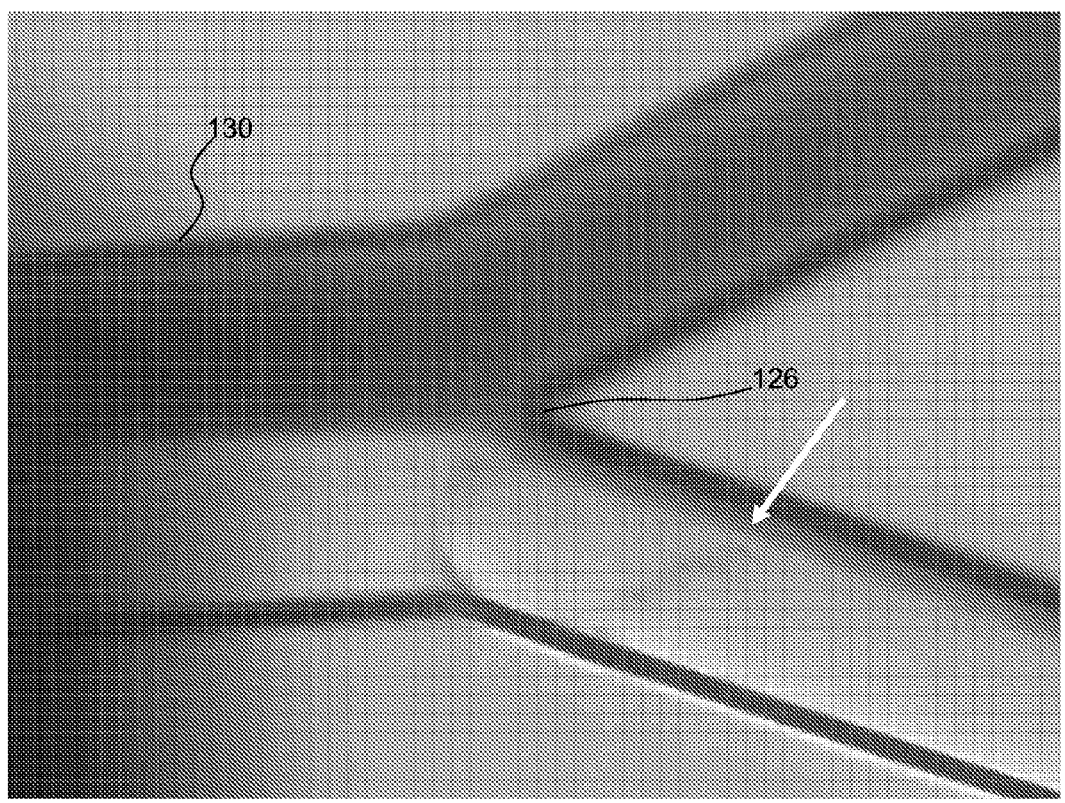
Figure 6:
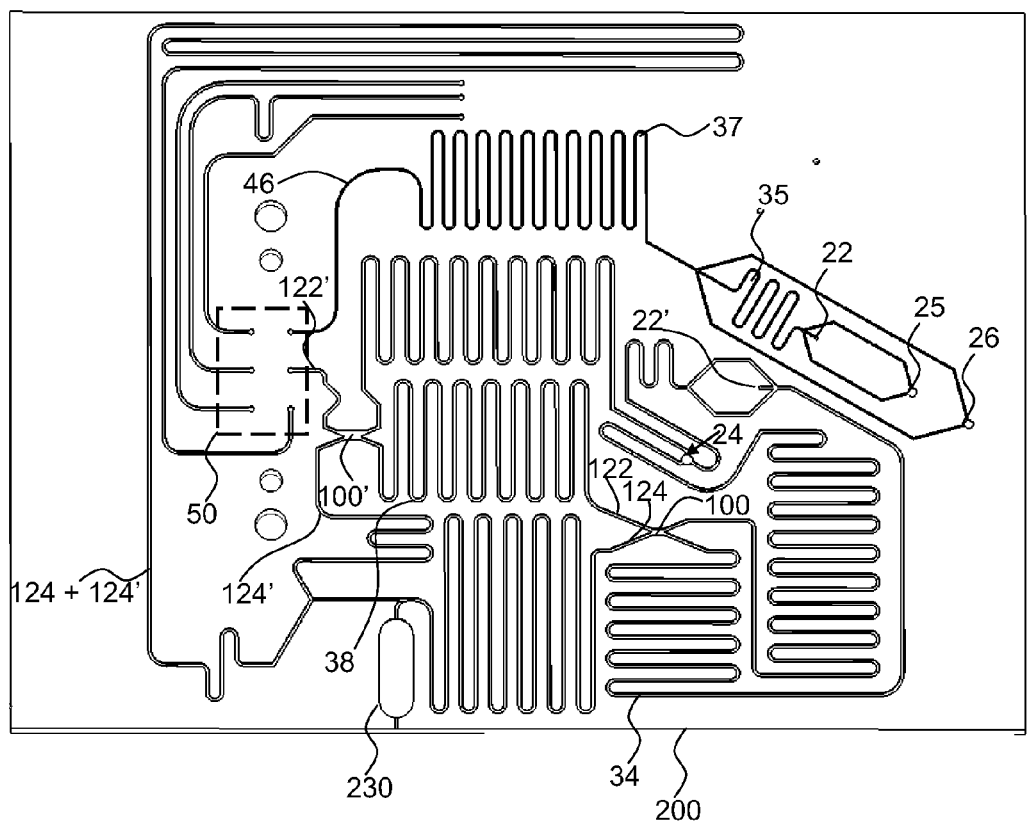

Embodiments of the invention are described in more detail and by way of non-limiting examples with reference to the accompanying drawings, wherein:

FIG. 1 schematically depicts a microfluidic device;

FIG. 2 schematically depicts an impedance measurement chip and the signal produced in such a chip;

FIG. 3 schematically depicts a prior art dilution stage;

FIG. 4 schematically depicts a dilution stage according to an embodiment of the present invention;

FIG. 5 shows a still from a video demonstrating the dilution principle of the present invention; and FIG. 6 schematically depicts a microfluidic device according to an embodiment of the present invention.

DETAILED DESCRIPTION OF THE DRAWINGS

It should be understood that the Figures are merely schematic and are not drawn to scale. It should also be understood that the same reference numerals are used throughout the Figures to indicate the same or similar parts.

The present invention relates to microfluidic devices including a microfluidic resistance network and a measurement stage as a single component, as well as to microfluidic devices that may comprise a plurality of discrete components, in particular a micro fluidic resistance network, which may be in the form of a disposable cartridge, and a separate measurement chip. The micro fluidic resistance network has the purpose of sample preparation and presenting the prepared sample to the measurement chip. In the context of the present invention, the term 'micro fluidic' is to relate to the behavior, precise control and manipulation of fluids that are geometrically constrained to a small, typically sub-milliliter, scale volumes, e.g. µl, nl, pl, fl volumes.

FIG. 1 schematically depicts a non-limiting example of such a micro fluidic device 10, which includes a disposable microfluidic resistance network 20 and a measurement chip 50. The microfluidic resistance network 20 is designed to receive a sample such as a FBC sample at sample inlet 22. The microfluidic resistance network 20 further comprises a diluent inlet 24 for receiving a diluent, which is branched off in three different branches. A first branch is mixed with the sample at the sample inlet 22 and subsequently fed to a sample mixing or dilution stage 34, e.g. a snake stage, whereas a second branch is used to further dilute the sample at junction 36. The junction 36 is typically shaped in a particular manner to obtain a desired dilution ratio of the sample with the diluent, as for instance is explained in more detail in WO 2010/086786. A sample dilution stage 38, e.g. a microfluidic snake stage, is designed such that that the sample is in contact with the diluent for a predetermined period of time, e.g. a period of time necessary to complete the dilution of the sample and to provide the required fluidic resistance At junction 36, a substantial part of the diluted sample received from dilution stage 34 is fed to a waste channel 43, whereas a (small) fraction of the diluted sample is mixed with the diluent from the second branch of the diluent inlet 24 and fed to the sample dilution stage 38. At junction 40, the sample diluted in sample dilution stage 38 is again split in a portion fed to waste channel 44, with the remaining portion further diluted by the diluent received from the third branch of the diluent inlet 24 and subsequently fed via measurement channel 42 to the measurement chip 50. A snake stage (not shown) may be present between the junction 40 and the measurement chip 50 for the aforementioned reasons. Junction 40 is typically shaped in a particular manner to obtain a desired dilution ratio of the diluted sample received from the sample dilution stage 38 with the diluent. Suitable embodiments of diluent have for instance been disclosed in WO 2010/086786. As has been previously explained, the flow rates through the channels of these junctions that are to transport the fraction of the sample combined with the diluent must be reduced to such an extent that most of the sample is fed to waste, e.g. to waste channels 43 and 44 as shown in FIG. 1. This however increases the risk that bubbles get trapped in the low flow rate channels as previously explained.

The microfluidic device 10 shown in FIG. 1 is particularly suited for the treatment and subsequent analysis of a FBC sample. However, it will be understood by the skilled person that design of the microfluidic resistance network 20 may be altered to prepare different types of samples, e.g. urine or saliva samples, as well as samples for non-medical evaluation, e.g. environmental samples, food samples and so on.

FIG. 2 shows the impedance measurement chip 50 in more detail. A detailed description of such an impedance measurement arrangement can be found in "Impedance spectroscopy flow cytometry: on-chip label-free cell differentiation", Cheung, K., S. Gawad, and P. Renaud, Cytometry A, 2005. 65(2): p. 124-132. FIG. 2 shows a side view of the microfluidic channel through the chip 50 and a sample cell 80 passing between the excitation electrodes 52, 62 and the detection electrodes 54, 64. The excitation electrode 52 and the detection electrode 54 form a first electrode pair and the excitation electrode 62 and the detection electrode 64 form a second electrode pair.

The excitation electrodes 52 and 62 are respectively connected to a current input signal source 58 and 68, e.g. an AC or DC input signal source. An AC input signal source is preferred as it prevents electrolysis at the electrodes. In an embodiment, the excitation electrodes 52 and 62 may share the same AC input signal source (i.e. 58=68). The detection electrodes are typically connected to a differential potential detection circuit 70, which preferably keeps the detection electrodes at an approximate ground potential. The currents passing through the fluid between the first and second electrode pair are amplified and its difference is determined in any suitable manner, e.g. using well-known analog electronics. The in-phase and out-of-phase parts of the resulting (AC) signal are measured using standard Lock-in-technology. Without a particle passing the electrodes the measured signal is ideally zero, although in practice always an offset is present due chip asymmetry, and potentially electronic component inaccuracies. If a particle coming from the left first passes the first electrode pair, a positive almost Gaussian shape signal is produced as the second electrode pair acts as the reference electrode for the first electrode pair. When the particle subsequently passes the second electrode pair, a negative Gaussian shape signal is produced, as the first electrode pair acts as the reference electrode for the second electrode pair. The resulting antisymmetric double Gaussian signal shape is also shown in FIG. 2. The Cell Signal may be the output of a Lock-In Amplifier measuring the current difference between both electrode pairs. In this way impedance spectroscopy can be performed for different cells, e.g. RBC or WBC.

The dilution of sample with a diluent in the microfluidic resistance network 20 of the microfluidic device 10 is typically achieved as shown in FIG. 3. A first microfluidic channel 82, e.g. for receiving a blood sample, is in fluidic communication with sample inlet 22. The first microfluidic channel 82 comprises a branch 83 that connects the first microfluidic channel 82 to a second micro fluidic channel 84 that is in fluidic communication with the diluent inlet 24. The microfluidic resistance network 20 is tuned such that only a fraction of the sample is diverted from the first microfluidic channel 82 into the second microfluidic channel 84. This may be achieved by tuning the resistances along all the other lines of the network, and the resulting pressure differences in equilibrium with the flows and resistances. FIG. 3 shows some exemplary flow rates of the fluids through the prior art dilution stage. The flow rates (in µl/s) are specified at the head of each arrow indicating the direction of the fluid flow. Hence, it can be seen in FIG. 3 that only 1% of the flow of the sample through the first microfluidic channel 82 is diverted into the second microfluidic channel 84 by the tuning of the microfluidic resistance network 20. The bulk of the sample (99% in the example of FIG. 3) is typically unused and fed to waste as indicated by the 39.6 µl/s flow rate in the first microfluidic channel 82 downstream from the branch 83.

A problem with such a dilution stage is that bubble trapping in the branch 83 at starting up the microfluidic resistance network 20 from a dry state is difficult to avoid due to the fact that the network 20 is tuned to produce a small flow rate only through the branch 83, e.g., 0.4 µl/s as shown in the example in FIG. 3, either by providing a branch 83 having smaller dimensions than the branches 82 and 84, or by providing a small pressure drop across the branch 83.

The present invention has addressed this problem by the provision of a novel and inventive dilution stage design, an example embodiment of which is shown in FIG. 4. Contrary to the prior art dilution stage design shown in FIG. 3, in the dilution stage of the present invention it is not necessary to separate a fraction of the fluid to be diluted, e.g. the sample prior to feeding this fraction to the dilution stage. Instead, the cross-shaped (i.e. X-shaped) dilution stage 100 comprises a first inlet formed by the first micro fluidic channel 112, e.g. a sample channel, and a second inlet formed by the second microfluidic channel 114, e.g. a diluent channel. The first micro fluidic channel 112 and the second microfluidic channel 114 define a first junction 110 of the dilution stage 100, in which a central point 116 defines the intersection between the first microfluidic channel 112 and the second microfluidic channel 114; in other words, the central point 116 defines the point where the sidewalls of the first micro fluidic channel 112 and the second microfluidic channel 114 meet. For the sake of completeness it is noted that the first microfluidic channel 112 is in fluidic communication with an inlet 22 and the second microfluidic channel 114 in fluidic communication with an inlet 24 such as the sample inlet and the diluent inlet of the microfluidic resistance network 20 shown in FIG. 1.

An imaginary axis 118 dissects the angle $\alpha$ between the first microfluidic channel 112 and the second microfluidic channel 114, i.e. divides $\alpha$ such that the angle between the imaginary axis 118 and either of the first micro fluidic channel 112 and the second micro fluidic channel 114 is $\alpha/2$. It is noted that the first microfluidic channel 112 and the second microfluidic channel 114 may have different dimensions in case a different flow rate through the first microfluidic channel 112 and the second microfluidic channel 114 is required. It is however preferable that the ratio of the flow rates through the first micro fluidic channel 112 and the second microfluidic channel 114 respectively lies in the range of 5:1-1:5 for flow rates that are in the µ/s domain as it has been found that for ratios outside this range the risk of bubble trapping again increases due to the fact that the microfluidic channel with the smaller flow rate becomes prone to promoting such bubble trapping.

The imaginary axis 118 defines the boundary between the first fluid, e.g. a blood sample or another suitable sample, flowing from the first microfluidic channel 112 and the second fluid, e.g. a diluent, flowing from the second microfluidic channel 114. It is important to realize that the dilution stage 100 is dimensioned such that diffusion of the first fluid into the second fluid and vice versa is negligible, i.e. no (significant) mixing of the two fluid streams occurs. Consequently, a well-defined interface is maintained between the first and second fluids through the dilution stage 100, which interface coincides with the imaginary axis 118.

The dilution stage 100 further comprises a second junction 120, which is positioned opposite to the first junction 110. The second junction comprises a first microfluidic outlet channel 122 and a second microfluidic outlet channel 124, in which a central point 126 defines the intersection between the first microfluidic outlet channel 122 and the second micro fluidic outlet channel 124; in other words, the central point 126 defines the point where the sidewalls of the first micro fluidic outlet channel 122 and the second microfluidic outlet channel 124 meet. The first microfluidic outlet channel 122 may have a different dimension to the second microfluidic outlet channel 124 in case the first microfluidic outlet channel 122 and the second microfluidic outlet channel 124 are to produce different outlet flow rates. Again, the ratio between these flow rates preferably lies in the range of 5:1-1:5 for outlet flow rates in the μl/s domain as it has been found that for ratios outside this range the risk of bubble trapping again increases due to the fact that the microfluidic outlet channel with the smaller flow rate becomes more sensitive to such bubble trapping.

In order to divert a fraction of the first fluid into the first microfluidic outlet channel 122, the central point 126 is displaced with respect to the imaginary axis 118 such that the central point 126 lies inside the path of the fluid stream originating from the first microfluidic channel 112, e.g. a blood sample. The central point 126 consequently acts as wedge in the first fluid stream by diverting a fraction of the first fluid stream into the first microfluidic outlet channel 122 whereas the remainder of the first fluid stream is diverted into the second microfluidic outlet channel 124. The value of offset parameter r (i.e. offset distance r) as shown in FIG. 4 defines the size of the fraction of the first fluid originating from the first micro fluidic channel 112 that is diverted into the first microfluidic outlet channel 122. It will be understood that the second fluid stream originating from the second microfluidic channel 114, e.g. a diluent, is completely fed into the first microfluidic outlet channel 122 as the position of the central point 126 does not interfere with this fluid flow.

The dilution stage 100 may optionally comprise an intermediate section 130 that separates the first junction 110 from the second junction 120. Such an intermediate section 130 can be useful in ensuring that the flow profile of the fluid flows through the dilution stage 100 reaches equilibrium. The length of the intermediate section 130, i.e. the separation distance between the first junction 110 and the second junction 120 should preferably be chosen such that diffusion of the first fluid into the second fluid and vice versa is negligible.

At this point, it is emphasized that the embodiment of the cross-shaped junction 100 shown in FIG. 4 is a non-limiting example of the present invention. The particular design shown in FIG. 4, i.e. using an offset between the first junction 110 and the second junction 120 to divert part of the sample into the first microfluidic outlet channel 122 is particularly suited for junctions in which a relatively high flow rate is to be maintained, e.g. flow rates for which Re is at least around 1. For smaller flow rates (Re<<1), the offset between the junctions 110 and 120 may be omitted, and the required portion of the sample to be diverted into the first microfluidic outlet channel 122 may be accurately defined by the tuning of the pressure (resistance) in the respective channels of the micro fluidic resistance network 20 comprising the cross-shaped junction 100.

FIG. 5 shows a frame from a video of a dilution stage 100 according to an embodiment of the present invention. Only the intermediate stage 130 and the second junction 120 are shown for the sake of clarity. As can be seen in FIG. 5, a dark fluid stream (blood) and a light fluid stream (a diluent formed by a filtered saline buffer) flow side-by-side through the intermediate stage 130 without mixing in this stage. The central point 126 of the second junction 120 is located inside the blood stream, such that a small fraction of the blood sample is diverted into the bottom microfluidic outlet channel together with the complete diluent flow. The fraction of the blood sample is indicated by the white arrow in FIG. 5. It has been found that the diverted flow of the blood sample maintained a constant flow rate throughout the duration of the dilution experiment captured on video, which was approximately 35 s, thereby clearly demonstrating the accuracy of the dilution stage 100 of the micro fluidic resistance network 20 of the present invention.

The microfluidic resistance network 20 including one or more dilution stages 100 may be incorporated in any suitable microfluidic device, such as the microfluidic device disclosed in WO 2010/086786. A non-limiting example of a microfluidic device 200 in accordance with an embodiment of the present invention is shown in FIG. 6. The microfluidic device 200 is designed to perform a FBC on a single blood sample. To this end, the microfluidic device 200 comprises a first blood sample input 22 into a WBC lysis stage for lysing red blood cells as shown in FIG. 1, including an inlet 25 for receiving a WBC lysing agent such as a formic acid/saponin mixture, and an inlet 26 for receiving a quenching agent for quenching the lysed sample to protect the white blood cells from lysing. A non-limiting example of a suitable quenching agent is a $NaCl/NaHCO_3$ solution. The lysing stage may comprise any suitable number of snake stages. Two snake stages 35 and 37 are shown by way of non-limiting example. The outlet channel 46 of the lysing stage is fed into the measurement chip 50, which by way of non-limiting example may be a measurement chip as shown in FIG. 2, having two measurement channels for a WBC count and a RBC/platelet analysis respectively.

The microfluidic device 200 further comprises a second blood sample inlet 22', which is fed into a red blood cell/platelet treatment stage. The first blood sample inlet 22 and the second blood sample inlet 22' may be separate branches of a single blood sample inlet (not shown) or may be independently fed with separate blood samples, e.g. separate portions of the same blood sample. The blood cell/platelet treatment stage further comprises a diluent sample inlet 24, which is split into a number of branches. Three branches are shown by way of non-limiting example; it should be understood that any suitable number may be chosen. A first branch is fed to the blood sample inlet 22' where the incoming blood sample is diluted by a predefined ratio, e.g. 20:1, and the second and third branch are fed to embodiments of the cross-shaped junctions of the present invention, i.e. junctions 100 and 100' respectively, where the diluent is mixed with blood sample. Two such serially connected junctions are shown, although it again should be appreciated that the chain of serially connected cross-shaped junctions of the present invention may comprise any suitable number of such junctions. Consequently, large dilution ratios can be achieved with only a small amount of diluent as no diluent is wasted in the microfluidic device 200.

Each of the junctions 100 and 100' has a first output, i.e. outputs 122 and 122' respectively, for generating a mixture of the small fraction of the incoming sample with all of the incoming diluent, and a second output 124 and 124' respectively for generating a waste stream essentially comprising of a large fraction of the incoming sample only. The mixing ratios in these junctions 100 and 100' may be achieved as previously explained in more detail with the aid of FIGS. 4 and 5. The various fluidic channels may contain one or more snake stages, e.g. stages 34 and 38, which may be included to tune the mixing ratio and the fluidic resistance of the fluidic channel, as is known per se. The sample output 122 of the junction 100' is fed to a sample channel of the measurement chip 50 for measuring a red blood cell count, whereas the waste outputs 124 and 124' of the junctions 100 and 100' are combined and fed to waste. In FIG. 6, the combined waste channel is also fed through the measurement chip 50, but this is entirely optional.

In FIG. 6, the waste channel 124 from the first junction 100 is branched off towards to a Hb sample chamber 230 including an optical measurement cell for preparing the unused portion of the blood sample for a Hb absorption measurement. The Hb sample chamber may contain some reagents in dry form that lyse and label the blood sample to perform the Hb measurement. In this arrangement, only a small sample of blood needs to be labeled for the Hb absorption measurement, which is advantageous as the labeling reagents can be toxic, e.g. comprise cyanide, as necessarily they must bind to Hb.

It is pointed out that FIG. 6 shows a non-limiting example of a microfluidic device 200 of the present invention. The microfluidic device 200 may for instance be a microfluidic device as described in detail in WO2010/086786. In FIG. 6, a part of the sample is branched off the RBC count preparation stage for Hb measurement preparation in the preparation stage 230. It will be understood that it is equally feasible to branch off part of the sample from the WBC count preparation stage for Hb sample preparation instead. The microfluidic device 200 may alternatively be arranged to generate three separate branches from the blood sample inlet 22, i.e. one branch for RBC/platelet count sample preparation, one branch for WBC sample preparation and one branch for Hb measurement sample preparation. Other variations will be apparent to the skilled person. The measurement chip 50 may for instance be an impedance measurement chip 50, which may be a separate component, such that the micro fluidic resistance network 20 and the impedance measurement chip 50 may be manufactured in different manufacturing processes. This is preferable from a cost-perspective, because the resolution required for the impedance measurement chip 50 is typically higher than the resolution required for the micro fluidic resistance network 20. The measurement chip 50, which may comprise an electrode arrangement as shown in FIG. 2, is preferably realized in a glass substrate, whereas the microfluidic resistance network 20 is preferably realized as a disposable cartridge in a polymer material. However, it is equally feasible to manufacture the measurement chip 50 in the same process as the micro fluidic resistance network 20.

The second microfluidic outlet channel 124' of the dilution stage 100' may comprise a matching element (not shown) to match the fluidic resistance of the second microfluidic outlet channel 124 to the sample channel through the measurement chip 50, such that the first microfluidic outlet channel 122 and the second microfluidic channel 124 exhibit fluidic resistances in the same order of magnitude. This is necessary because the dimensions of the sample channel through the measurement chip 50 are typically smaller than the dimensions of the first microfluidic outlet channel 122 and the second microfluidic outlet channel 124, such that without such a matching element substantially all of the sample and diluent would be forced into the waste channel, i.e. the second microfluidic channel 124'.

It is pointed out that FIG. 6 shows a non-limiting example of a microfluidic device 200 of the present invention. Although the preferred application domain of the microfluidic resistance network 20 of the present invention is FBC analysis in human or veterinary diagnostics, the present invention is not limited to such application domains. The microfluidic resistance network of the present invention may be applied in any suitable application domain, e.g. in microfluidic devices for environmental sample analysis or food sample analysis by way of non-limiting example.

It should furthermore be understood that the microfluidic resistance network 20 preferably is a tuned microfluidic resistance network 20, i.e. a network in which the dimensions of the various components of the microfluidic resistance network 20 are designed to achieve well-defined flow rates through these components. This has the advantage that such a microfluidic resistance network 20 can be operated using a minimal number of pumps as the flow rates of the various fluid streams do not need to be controlled by pumps.

It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting the claim. The word "comprising" does not exclude the presence of elements or steps other than those listed in a claim. The word "a" or "an" preceding an element does not exclude the presence of a plurality of such elements. The invention can be implemented by means of hardware comprising several distinct elements. In the device claim enumerating several means, several of these means can be embodied by one and the same item of hardware. The mere fact that certain measures are recited in mutually different dependent claims does not indicate that a combination of these measures cannot be used to advantage.

The invention claimed is:

1. A microfluidic resistance network comprising:
a first microfluidic channel in fluidic communication with a first fluid inlet; and
a second microfluidic channel in fluidic communication with a second fluid inlet; wherein the microfluidic resistance network further comprises a cross-shaped dilution stage having the first microfluidic channel as a first dilution stage inlet and the second microfluidic channel as a second dilution stage inlet, the first dilution stage inlet and the second dilution stage inlet forming a first junction; and
the dilution stage further comprising:
a first microfluidic outlet channel for combining a portion of a first fluid from the first microfluidic channel with a second fluid from the second microfluidic channel and;
a second microfluidic outlet channel for receiving the remainder of first fluid, the first microfluidic outlet and the second microfluidic outlet forming a second junction opposite the first junction, wherein a central point defines the intersection between the first microfluidic outlet and the second microfluidic outlet.

2. The microfluidic resistance network of claim 1, wherein the first fluid is a sample and the second fluid is a diluent.

3. The microfluidic resistance network of claim 1, wherein the ratio between the combined portion of the first fluid from the first microfluidic channel with the second fluid from the second microfluidic channel on the one hand and the remainder of first fluid on the other hand is at least partially defined by the pressure in the microfluidic resistance network.

4. The microfluidic resistance network of claim 1, wherein the cross-shaped dilution stage further comprises an intermediate section coupling the first junction to the second junction.

5. The microfluidic resistance network of claim 4, wherein the intermediate section has a length extending from the first junction to the second junction such that diffusion between the sample and the diluent is negligible in said intermediate section.

6. The microfluidic resistance network of claim 1, wherein the network is tuned such that in operation the ratio of the respective flow rates of the first fluid and the second fluid entering the cross-shaped dilution stage is in the range of 1:5-5:1.

7. The microfluidic resistance network of claim 1, wherein the first microfluidic outlet channel is in fluidic communication with a mixing stage downstream from the cross-shaped dilution stage.

8. The microfluidic resistance network of claim 1, wherein:
said first junction comprises a central point where the respective sidewalls of the first microfluidic channel and the second microfluidic channel meet, wherein an imaginary axis through said central point dissects the angle between the first microfluidic channel and the second microfluidic channel; and
wherein said central point at said second junction is being displaced with respect to said imaginary axis by a predefined distance.

9. The microfluidic resistance network of claim 1, wherein the cross-shaped dilution stage is one of a chain of serially connected cross-shaped dilution stages, and wherein the second microfluidic channel comprises a plurality of branches, each of said branches providing one of the inlets of one of the cross-shaped dilution stages in said chain, wherein the other inlet of the first cross-shaped dilution stage in said chain is coupled to the first microfluidic channel, and the other inlet of each of the remaining cross-shaped dilution stages is coupled to the first microfluidic outlet channel of the previous cross-shaped dilution stage in said chain.

10. A disposable cartridge for a body fluid analysis system, the disposable cartridge comprising the microfluidic resistance network of claim 1.

11. A microfluidic device comprising:
a microfluidic resistance network comprising:
a first microfluidic channel in fluidic communication with a first fluid inlet; and
a second microfluidic channel in fluidic communication with a second fluid inlet, wherein the microfluidic resistance network further comprises a cross-shaped dilution stage having the first microfluidic channel as a first dilution stage inlet and the second microfluidic channel as a second dilution stage inlet, the first dilution stage inlet and the second dilution stage inlet forming a first junction; and
the dilution stage further comprising:
a first microfluidic outlet channel for combining a portion of a first fluid from the first microfluidic channel with a second fluid from the second microfluidic channel and;
a second microfluidic outlet channel for receiving the remainder of first fluid, the first microfluidic outlet and the second microfluidic outlet forming a second junction opposite the first junction, wherein a central point defines the intersection between the first microfluidic outlet and the second microfluidic outlet; and
a measurement device comprising a sample channel in fluidic communication with the first microfluidic outlet channel, the sample channel comprising measurement means.

12. The microfluidic device of claim 11, wherein the measurement means comprise a first electrode pair and a second electrode pair downstream from the first electrode pair for performing an impedance measurement.

13. The microfluidic device of claim 11, wherein the microfluidic device is adapted to perform a bodily fluid analysis.

14. The microfluidic device of claim 11, further comprising an optical measurement cell for measuring a hemoglobin count.

15. The microfluidic device of claim 11, wherein the microfluidic resistance network is comprised in a disposable cartridge.

* * * * *